United States Patent [19]

Schönafinger et al.

[11] Patent Number: 5,091,398
[45] Date of Patent: Feb. 25, 1992

[54] SUBSTITUTED 1,2,3,4-OXATRIAZOLIUM-5-OLATES, A PROCESS FOR THEIR PREPARATION AND THEIR USE

[75] Inventors: Karl Schönafinger, Alzenau; Helmut Bohn, Schöneck; Rudi Beyerle, Frankfurt; Melitta Just, Nidderau, all of Fed. Rep. of Germany

[73] Assignee: Cassella Aktiengellschaft, Frankfurt, Fed. Rep. of Germany

[21] Appl. No.: 506,441

[22] Filed: Apr. 6, 1990

[30] Foreign Application Priority Data

Apr. 10, 1989 [DE] Fed. Rep. of Germany ....... 3911668

[51] Int. Cl.⁵ .................... C07D 273/01; A61K 31/41
[52] U.S. Cl. ....................................... 514/361; 548/125
[58] Field of Search ......................... 548/125; 514/361

[56] References Cited

U.S. PATENT DOCUMENTS 3,427,317 7/1969 Kier ..................................... 548/125

OTHER PUBLICATIONS

Kier, J. Pharm. Sci. 55 1467 (1966).

Primary Examiner—Robert Gerstl
Attorney, Agent, or Firm—Perman & Green

[57] ABSTRACT

The 1,2,3,4-oxatriazolium-5-olates of the formula I

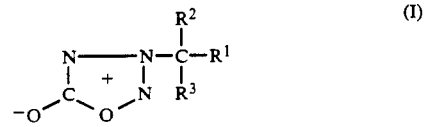

in which
R¹ denotes, for example, ($C_2$ to $C_4$)alkyl,
R² and R³ denotes ($C_1$ to $C_4$)alkyl have useful pharmacological properties.

9 Claims, No Drawings

SUBSTITUTED 1,2,3,4-OXATRIAZOLIUM-5-OLATES, A PROCESS FOR THEIR PREPARATION AND THEIR USE

The invention relates to novel 1,2,3,4-oxatriazolium-5-olates substituted in the 3-position, of the general formula I $$\begin{array}{c} R^2 \\ | \\ N\!\!-\!\!-\!\!-\!\!N\!\!-\!\!C\!\!-\!\!R^1 \\ | \quad + \quad | \\ \phantom{-}C\phantom{-}\phantom{O}N\phantom{-}R^3 \\ -O\phantom{-}\phantom{O} \end{array} \quad (I)$$

in which
  $R^1$ denotes ($D_2$ to $D_4$)alkyl or $-CONR^4R^5$,
  $R^2$ and $R^3$, independently of one another, denote ($C_1$ to $C_4$)alkyl,
  $R^4$ denotes hydrogen or ($C_1$ to $C_4$)alkyl,
  $R^5$ denotes ($C_1$ to $C_4$)alkyl or
  $R^4$ and $R^5$, together with the nitrogen atom to which they are bonded, denote a heterocyclic ring.

The invention also relates to a process for the preparation of the compounds of the formula I and to their use.

The formula Ia $$\begin{array}{c} R^2 \\ | \\ N\!\!-\!\!-\!\!-\!\!N\!\!-\!\!C\!\!-\!\!R^1 \\ | \quad \pm \quad | \\ C\phantom{-}\phantom{O}N\phantom{-}R^3 \\ O=\phantom{-}\phantom{-}O \end{array} \quad (Ia)$$

and mesomeric boundary structures, for example those of the formulae Ib to If:

$$\begin{array}{c} R^2 \\ | \\ \overset{-}{N}\!\!-\!\!-\!\!-\!\!\overset{+}{N}\!\!-\!\!C\!\!-\!\!R^1 \\ | \quad \quad || \\ C\phantom{-}\phantom{O}N\phantom{-}R^3 \\ O=\phantom{-}\phantom{-}O \end{array} \quad (Ib)$$

$$\begin{array}{c} R^2 \\ | \\ N\!\!=\!\!=\!\!\overset{+}{N}\!\!-\!\!C\!\!-\!\!R^1 \\ | \quad \quad || \\ C\phantom{-}\phantom{O}N\phantom{-}R^3 \\ -O\phantom{-}\phantom{O} \end{array} \quad (Ic)$$

$$\begin{array}{c} R^2 \\ | \\ \overset{-}{N}\!\!-\!\!-\!\!-\!\!N\!\!-\!\!C\!\!-\!\!R^1 \\ | \quad \quad | \\ C\phantom{-}\phantom{O}N\phantom{-}R^3 \\ O=\phantom{-}\phantom{-}O \\ \phantom{O}+ \end{array} \quad (Id)$$

$$\begin{array}{c} R^2 \\ | \\ N\!\!=\!\!=\!\!N\!\!-\!\!C\!\!-\!\!R^1 \\ || \quad \quad | \\ C\phantom{-}\phantom{O}N\phantom{-}R^3 \\ -O\phantom{-}\phantom{O} \\ \phantom{O}+ \end{array} \quad (Ie)$$

$$\begin{array}{c} R^2 \\ + | \\ N\!\!=\!\!=\!\!=\!\!\overset{+}{N}\!\!-\!\!C\!\!-\!\!R^1 \\ | \quad \quad | \\ C\phantom{-}\phantom{O}N^-\phantom{-}R^3 \\ O=\phantom{-}\phantom{-}O \end{array} \quad (If)$$

can also be given for the compounds of the formula I.

The alkyl radicals represented by $R^1$, $R^2$, $R^3$, $R^4$ and $R^5$ may be straight-chain or branched.

Examples of ($C_2$ to $C_4$)alkyl radicals which can be represented by $R^1$, $R^2$, $R^3$, $R^4$ and $R^5$ are ethyl, propyl, i-propyl, butyl, i-butyl, sec-butyl or tert-butyl. For $R^2$, $R^3$, $R^4$ and $R^5$, methyl is in addition also possible. $R^2$ and $R^3$ may be identical or different and preferably denote ethyl or methyl and are preferably identical. $R^2$ and $R^3$ very particularly preferably both denote methyl.

The ($C_2$ to $C_4$)alkyl radicals are preferred for $R^1$, the ethyl radical is very particularly preferred for $R^1$.

The alkyl radicals represented by $R^2$, $R^3$, $R^4$ and/or $R^5$ are preferably unbranched. Examples of the radicals $-CONR^4R^5$ represented by $R^1$ are: methylaminocarbonyl, ethylaminocarbonyl, i-propylaminocarbonyl, i-butylaminocarbonyl, N,N-diethylaminocarbonyl, N,N-dimethylaminocarbonyl, N,N-di-n-propylaminocarbonyl and N,N-di-n-butylaminocarbonyl.

$R^4$ and $R^5$, together with the nitrogen atom to which they are bonded, can form a heterocyclic ring, in particular a 5-, 6- or 7-membered heterocyclic ring, which may also contain one or more heteroatoms from the series comprising N, O or S. For example, $R^4$ and $R^5$, together with the nitrogen atom to which they are bonded, can form a pyrrolidine, piperidine, piperazine or morpholine radical.

The compounds of the general formula I can be prepared by cyclization of nitroso compounds of the general formula II $$\begin{array}{c} \phantom{XX}O \quad O\!=\!N \quad R^2 \\ \phantom{XX}|| \quad\quad | \quad\quad | \\ H_2N\!-\!C\!-\!NH\!-\!N\!-\!C\!-\!R^1 \\ \phantom{XXXXXXXXXXXX}| \\ \phantom{XXXXXXXXXXXX}R^3 \end{array} \quad (II)$$

in which $R^1$, $R^2$ and $R^3$ have the meanings already mentioned.

The cyclization of the compounds of the formula II is carried out in a solvent by heating to 30 to the boiling point of the solvent, in particular 30° to 100° C., preferably 50° to 80° C., and can be accelerated by addition of an acid.

Suitable solvents are, for example: water; alcohols, in particular those having 1 to 6 C atoms, such as, for example, methanol, ethanol, i- and n-propanol, i-, sec- and tert-butanol, n-, i-, sec- and tert-pentanol, n-hexanol, cyclopentanol, cyclohexanol; ethers, in particular those having 2 to 8 C atoms in the molecule, such as, for example, diethyl ether, methyl ethyl ether, di-n-propyl ether, di-isopropyl ether, methyl n-butyl ether, ethyl propyl ether, dibutyl ether, tetrahydrofuran, 1,4-dioxane, 1,2-dimethoxyethane, bis-$\beta$-methoxyethyl ether; polyethers, such as, for example, polyethylene glycols having a molecular weight up to about 600, glycols and partially etherified glycols, such as, for example, ethylene glycol, propylene glycol, trimethylene glycol, ethylene glycol monomethyl ether, ethylene glycol monoethyl ether, diethylene glycol monoethyl ether; ketones, in particular those having 3 to 10 C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, benzophenone, acetophenone; aliphatic hydrocarbons, such as, for example, low- and high-boiling petroleum ethers; aromatic hydrocarbons, such as, for example, benzene, toluene, o-, m- and p-xylene; halogenated aliphatic or aromatic hydrocarbons, such as, for example, methylene chloride, chloroform, carbon tetrachloride, ethylene chloride, chlorobenzene, dichlorobenzene; nitriles, such as, for example, acetonitrile; amides, such as, for example, dimethylformamide, N-methyl-pyrrolidone; and sulphoxides, such as, for example, dimethyl sulphoxide.

The cyclization can also be carried out in a mixture of different solvents.

Suitable acids for accelerating the cyclization are organic or inorganic acids. Suitable organic acids are, for example, unsubstituted or substituted aliphatic or aromatic carboxylic acids, such as, for example, formic acid, acetic acid, propionic acid, butyric acid; furthermore fluoroacetic acid, difluoroacetic acid, trifluoroacetic acid, glycolic acid, chloroacetic acid, dichloroacetic acid, trichloroacetic acid, α-chloropropionic acid, β-chloropropionic acid, benzoic acid, o-, m- or p-toluic acid, o-, m- or p-chlorobenzoic acid, or o-, m- or p-nitrobenzoic acid.

Suitable inorganic acids are, for example, sulphuric acid; hydrohalic acids, in particular hydrochloric acid; and phosphoric acid. Furthermore, for example, sulphonic acids, such as, for example, benzenesulphonic acid, p-toluenesulphonic acid or methanesulphonic acid, are suitable.

By means of addition of an acid, the cyclization of the compounds of the formula II can be accelerated under certain circumstances so that heating to relatively high temperatures is no longer necessary for the cyclization, as the cyclization already proceeds at room temperature or relatively low temperatures.

With the addition of an acid, therefore, the cyclization can be carried out in a solvent at temperatures from 5° C. up to the boiling point of the solvent, preferably at temperatures from room temperature to 100° C., very particularly preferably from room temperature up to 80° C.

The acids used for accelerating the cyclization may also be used, if appropriate, as solvents, thus, for example, acetic acid or hydrochloric acid.

The nitroso compounds of the formula II can be prepared by nitrosylation of semicarbazides of the formula III with nitrous acid in a manner known per se:

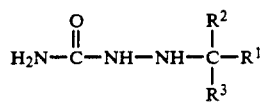  (III)

The semicarbazides of the formula III can be obtained from the corresponding hydrazines of the general formula IV

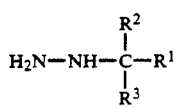  (IV)

in a manner known per se, for example by reaction with cyanates. The hydrazines of the formula IV can be obtained by monoalkylation of hydrazine or hydrazine hydrate with alkylating agents of the formula V

  (V)

according to methods known per se, where X denotes a halogen, for example bromine. In the formulae III to V, $R^1$, $R^2$ and $R^3$ have the meanings already mentioned at the beginning. The compounds of the formula V are known or can be prepared by known processes.

Similar compounds to the compounds according to the invention are described in GB 1,065,684, in part, as hypotensive and CNS-stimulating compounds.

The compounds of the formula I according to the invention possess useful pharmacological properties. It has surprisingly been found with the compounds of the formula I according to the invention that they display an antianginal effect and that they cause relief of the load on the heart in angina pectoris. In addition, these compounds display antithrombotic effects in animal models.

The compounds of the formula I according to the invention are therefore suitable for the preparation of medicaments having an antianginal or antithrombotic effect.

The compounds of the formula I can therefore be administered to humans as medicaments on their own, in mixtures with one another or in the form of pharmaceutical preparations which permit enteral or parenteral use and which contain an effective dose of at least one compound of the formula I, in addition to one or more customary pharmaceutically acceptable excipients or diluents and, if appropriate, one or more additives, as the active constituent.

The medicaments can be administered orally, for example in the form of tablets, film tablets, coated tablets, hard and soft gelatin capsules, microcapsules, granules, powders, pellets, solutions, syrups, emulsions, suspensions, aerosols, foams, pills or pastilles. However, administration can also be carried out rectally, for example in the form of suppositories, or parenterally, for example in the form of injection solutions, or percutaneously, for example in the form of ointments, creams, gels, pastes, aerosols, foams, powders or tinctures.

The pharmaceutical preparations can be prepared in a manner known per se using pharmaceutically inert inorganic or organic auxiliaries, excipients, fillers or diluents. For the preparation of pills, tablets, film tablets, coated tablets and the pellet or granule fillings of hard gelatin capsules, calcium phosphates, lactose, sorbitol, mannitol, starches, prepared starches, chemically modified starches, starch hydrolysates, cellulose, cellulose derivatives, synthetic polymers, talc etc. can, for example, be used. Excipients or diluents for soft gelatin capsules and suppositories are, for example, fats, waxes, semisolid and liquid polyols, natural or solidified oils etc. Suitable excipients or diluents for the preparation of solutions and syrups are, for example, water, polyols, and solutions of sucrose, dextrose, glucose etc. Suitable excipients for the preparation of injection solutions are, for example, water, alcohols, glycerol, polyols or vegetable oils. Suitable excipients or diluents for ointments, creams and pastes are, for example, natural petroleum jelly, synthetic petroleum jelly, viscous and mobile paraffins, fats, natural or solidified vegetable and animal oils, neutral oils, waxes, wax alcohols, polyethyleneglycols, polyacrylic acid, silicone gels etc.

In addition to the active compounds and diluents, fillers or excipients, the pharmaceutical preparations may further also contain, in a manner known per se, one or more additives or auxiliaries, such as, for example, disintegrants, binders, glidants, lubricants, mould-release agents, wetting agents, stabilizers, emulsifiers, preservatives, sweeteners, colorants, flavourings or perfumes, buffer substances, and in addition solvents or solubilizers, solution accelerators, antifoam agents, salt-forming agents, gel-forming agents, thickeners, flow-regulating agents, absorbents, agents for achieving a depot effect or agents, in particular salts, for changing the osmotic pressure, coatings or antioxidants etc. They may also contain two or more compounds of the formula I and, in addition, one or more other therapeutically active substances.

Other therapeutically active substances of this type may be, for example: $\beta$-receptor blockers, such as, for example, propranolol, pindolol, metoprolol; vasodilators, such as, for example, carbochromene; tranquilizers, such as, for example, barbituric acid derivatives, 1,4-benzodiazepines and meprobamate; diuretics, such as, for example, chlorothiazide; cardiotonic agents, such as, for example, digitalis preparations, hypotensive agents, such as, for example, hydralazine, dihydralazine, prasosine, clonidine, Rauwolfia alkaloids; agents which lower the fatty acid level in the blood, such as, for example, benzafibrates, fenofibrates; and agents for thrombosis prophylaxis, such as, for example, phenprocoumon.

The content of the active compound or the active compounds of the formula I in the pharmaceutical preparations can vary within wide limits and is, for example, 0.05 to 50% by weight, preferably 0.05 to 20% by weight. In solid administration forms, such as coated tablets, tablets etc. the content of one or more active compounds of the formula I is in many cases 2 to 20% by weight. Liquid administration forms, such as drops, emulsions and injection solutions frequently contain 0.05 to 2% by weight, preferably 0.05 to 1% by weight, of one or more active compounds of the formula I. The content of one or more active compounds of the formula I may optionally be partially replaced in the pharmaceutical preparations, for example up to 50% by weight, preferably up to 5 to 40% by weight, by one or more other therapeutically active substances.

The compounds of the formula I and the pharmaceutical preparations which contain the compounds of the formula I as active compounds can be used in humans for the treatment or prevention of thromboses and of disorders of the cardiovascular system, for example as antihypertensive agents in the various forms of high blood pressure, and in the control or prevention of angina pectoris etc. The dosage may vary within wide limits and is to be tailored to the individual conditions in each individual case. In general, a daily dose of the active compound or active compound mixture of about 0.5 to 100 mg, preferably 1 to 20 mg per human individual is adequate for oral administration. For other administration forms, the daily dose, owing to the good absorption of the active compound, is also in similar ranges of amounts, i.e. in general also 0.5 to 100 mg/human. The daily dose is normally divided into several, for example 2 to 4, partial administrations.

The pharmacological effect of the compounds of the formula I was determined according to a modified method of Godfraind and Kaba (Arch. Int. Phamacodyn. Ther. 196, (Suppl) 35 to 49, 1972) and of Schüman et al. (Naunyn-Schmiedeberg's Arch. Phamacol. 289, 409 to 418, 1975). Spiral strips of the pulmonary artery of the guinea pig are depolarised with 40 mmol/1 of potassium after equilibration in calcium-free Tyrode solution. An addition of 0.5 mmol/1 of CaCl$_2$ then induces a contraction. The relaxing effect of the test substance is determined by cumulative addition in $\frac{1}{2}$ log 10 stepped concentrations. The concentration of the test substance which inhibits the contraction by 50% ($=$IC$_{50}$, mol/1) is determined from the concentration-effect curve (abscissa: $-$log mol/1 of test substance, ordinate: percentage inhibition of the maximum contraction, mean value of 4 to 6 vessel strips). The IC$_{50}$ values obtained are indicated in the following table. As the comparison with the IC$_{50}$ value $3.10^{-4}$ for the known compound molsidomine (N-ethoxycarbonyl-3-morpholinusydnoneimine) reveals, compare DE-B-1,695,897, the values for the compounds of the formula I are considerably more favourable.

TABLE

| Compounds of the formula I according to Example | IC$_{50}$ (mol/1) |
|---|---|
| 1 | $3.10^{-6}$ |
| 4 | $6.10^{-5}$ |
| 5 | $6.10^{-7}$ |
| Molsidomine (N-ethoxycarbonyl-3-morpholinosydnoneimine) Comparison substance | $>1.10^{-4}$ |

EXAMPLE 1

3-tert-Pentyl-1,2,3,4-oxatriazolium-5-olate a) tert-Pentylhydrazine

A mixture consisting of 68 g of hydrazine hydrate, 161 ml of water, 80 g of tert-pentyl alcohol and 31 g of conc. hydrochloric acid is heated at 60° C. for 3 h. After this time, the volatile components are distilled off up to the boiling point of 80° C. by using a distillation bridge. After cooling, the residue is washed using 100 ml of methylene chloride and rendered alkaline with potash and the product is extracted using methylene chloride. The methylene chloride phase is dried over sodium sulphate and concentrated.

Yield: 18 g of oil.

b) 1-tert-Pentyl semicarbazide 13.6 g of potassium cyanate are added to a mixture of 17 g of tert-pentylhydrazine and 30 ml of water cooled in an ice bath and 16.5 g of conc. hydrochloric acid are then added dropwise. The mixture is stirred at room temperature for 3 h and the solid is filtered off with suction, washed with water and dried in vacuo.

Yield: 12 g. m.p. 166 to 168° C.

c) 1-tert-Pentyl-1-nitroso semicarbazide 1-tert-Pentyl semicarbazide (12 g) in a mixture of 50 ml of water and 25 ml of methanol is cooled in an ice bath and 5.6 g of sodium nitrite are added. Conc. hydrochloric acid is added dropwise to this solution until a pH of 4 to 5 is established.

The reaction mixture is stirred overnight at room temperature. The precipitate is filtered off with suction and dried in vacuo.

Yield: 9.8 g . m.p. 111 to 113° C.

d) 3-tert-Pentyl-1,2,3,4-oxatriazolium-5-olate

The nitroso compound described above (9.8 g) is dissolved in 30 ml of chloroform. After adding 4 ml of glacial acetic acid, the solution is heated at 60° C. for 2 h. After cooling to room temperature the mixture is extracted by shaking three times with 30 ml of water each time and the chloroform phase is dried over sodium sulphate and evaporated. The oily residue is distilled in vacuo.

Yield: 5.1 g of oil. b.p.: 92 to 95° C. (at a pressure of 1.06 mbar)

EXAMPLE 2

3-(1-Methyl-1-morpholinocarbonylethyl)-1,2,3,4-oxatriazolium-5-olate a) 1-Hydrazinoisobutyric acid morpholide hydrochloride

A solution of 63 g of α-bromoisobutyric acid morpholide and 40 g of hydrazine hydrate in 250 ml of ethanol is heated at 70° C. for 24 h. The volatile components are distilled off in vacuo, 100 ml of water and 50 ml of conc. hydrochloric acid are added to the residue and the non-basic components are separated by shaking with methylene chloride. The aqueous phase is then neutralized using sodium hydroxide solution and a large quantity of potash is added. The product is extracted using methylene chloride. After drying and concentrating the organic phase, a yellowish oil remains. Yield: 17.9 g . m.p. (hydrochloride): 208 to 210° C.

b) 1-(1-Methyl-1-morpholinocarbonylethyl) semicarbazide

A solution of 10 g of the abovementioned oil and 4.3 g of potassium cyanate in 30 ml of water is neutralized using conc. hydrochloric acid and stirred at room temperature for 4 h. The formation of the novel product is followed by thin-layer chromatography (mobile phase methylene chloride: methanol=9:1; silica gel) and is complete after this time.

c) 1-Nitroso-1-(1-methyl-1-morpholinocarbonylethyl) semicarbazide 4.3 g of sodium nitrite are added to the reaction mixture obtained above, and a pH of 2 to 3 is established using conc. hydrochloric acid and cooling in an ice bath. The mixture is stirred at room temperature for 1 h and the nitroso compound is then extracted by shaking with ethyl acetate. After drying and concentrating, a resinous residue remains which is processed further without further purification.

d) 3-(1-Methyl-1-morpholinocarbonylethyl)-1,2,3,4-oxatriazolium-5-olate

The resinous product obtained above is stirred at room temperature for 6 h in 100 ml of 2N HCl. The solid is filtered off with suction, washed with water and dried in vacuo. Yield: 6.2 g m.p. 123 to 124° C.

EXAMPLE 3

3-(1-Methyl-1-piperidinocarbonylethyl)-1,2,3,4-oxatriazolium-5-olate

The precursors 3a) to 3c) required for the preparation of the compound are prepared analogously to Example 2a) to 2c). 3c) 1 Nitroso-1-(1-methyl-1-piperidinocarbonylethyl) semicarbazide m.p. 138 to 151° C.

3d)

3-(1-Methyl-1-piperidinocarbonylethyl)-1,2,3,4-oxatriazolium-5-olate

The compound 3c) (4.5 g) is suspended in 50 ml of water. Using conc. hydrochloric acid, a pH of 2 is established and the mixture is heated at 60° C. for 1 h. After cooling, the solid is filtered off with suction and recrystallized from isopropanol.

Yield: 2.4 g m.p.: 109 to 111° C.

EXAMPLE 4

3-(1-tert-Butylaminocarbonyl-1-methylethyl)-1,2,3,4-oxatriazolium-5-olate

The precursors 4a) to 4c) required for the preparation of the compound are prepared analogously to Example 2a) to 2c).

4c)

1-Nitroso-1-(1-tert-butylaminocarbonyl-1-methylethyl) semi-carbazide m.p. 165 to 166° C.

4d)

3-(1-tert-Butylaminocarbonyl-1-methylethyl)-1,2,3,4-oxatriazolium-5-olate

A mixture of 12.0 g of the compound 4c), 30 ml of glacial acetic acid and 70 ml of chloroform is heated under reflux for 3 h. After cooling to room temperature, it is washed with sodium bicarbonate solution and with water, and the chloroform solution is dried using sodium sulphate and concentrated. The residue is recrystallized from tert-butyl methyl ether.

Yield: 4.3 g , m.p. 119 to 120° C .

EXAMPLE 5

3-(2-Methylpent-2-yl)-1,2,3,4-oxatriazolium-5-olate a) (2-Methylpent-2-yl)hydrazine hydrochloride

Acetone azine (93 g) is added dropwise under reflux to a solution of propylmagnesium bromide, prepared from 44.3 g of magnesium and 224 g of propyl bromide in 350 ml of ether. After heating under reflux for 3 days, the mixture is poured into an ice-cooled aqueous ammonium chloride solution (500 ml) and the product is extracted using ether. The ether phase is concentrated, and the oily residue is stirred at room temperature for 2 h in 200 ml of water and 100 ml of conc. hydrochloric acid. The non-basic components are removed using tert-butyl methyl ether and the aqueous solution is concentrated on a rotary evaporator.

Yield: 24.2 g (crude product)

b) 1-(2-Methylpent-2-yl) semicarbazide

The crude product from Example 5a) is cooled to 0° C. in 75 ml of water, 14 g of potassium cyanate are added and the mixture is kept at room temperature for 20 h. This mixture is shaken with 50 ml of methylene chloride in each case at pH 2, 4 and 6 and the organic phases obtained at pH 4 and 6 are combined, dried and concentrated. Yield: 6 g (crude product)

c) 1-(2-Methylpent-2-yl)-1-nitroso semicarbazide

The crude product from Example 5b) is dissolved in 100 ml of water and 4 ml of conc. hydrochloric acid and cooled to 0° to 5° C., and 3.2 g of sodium nitrite are added to the resulting mixture, which is stirred at room temperature for 3 h. The nitroso compound is extracted using methylene chloride. The organic phase is dried and concentrated. Yield: 5.8 g of oil.

d) 3-(2-Methylpent-2-yl)-1,2,3,4-oxatriazolium-5-olate 2.4 g of glacial acetic acid are added to a solution of 5 g of the oil from Example 5c) in 50 ml of ethyl acetate and the mixture is heated at 60° C. for 2 h. After cooling, it is washed using 3 portions of water for each 50 ml and the ethyl acetate phase is dried over sodium sulphate and concentrated. The oily residue is purified by column chromatography (silica gel, eluent: methylene chloride). The clean fractions are combined and concentrated.

Yield: 3.9 g. m.p. 30° to 32° C.

EXAMPLE 6

The compound 3-(3-methylpent-3-yl)-1,2,3,4-oxatriazolium-5-olate is prepared analogously to Example 5 in the form of an oil.

EXAMPLE 7

The compound 3-(2,3-dimethyl-but-2-yl)-1,2,3,4-oxatriazolium-5-olate is prepared analogously to Example 5.

m.p.: 38° C.

Pharmaceutical preparations are described in the following examples:

EXAMPLE A

Emulsions containing 3 mg of active compound per 5 ml can be prepared by the following recipe:

| | |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.2 to 2 g |
| Flavouring | q.s. |
| Water (demineralized or distilled) to | 100 ml |

EXAMPLE B

Coated tablets can be prepared by the following recipes:

| | | |
|---|---|---|
| (a) Active compound | 46 mg | |
| Lactose | 90 mg | |
| Maize starch | 90 mg | |
| sec calcium phosphate | 34 mg | |
| Soluble starch | 3 mg | |
| Magnesium stearate | 3 mg | |
| Colloidal silica | 4 mg | |
| | 270 mg | |
| (b) Active compound | 10 mg | |
| Lactose | 60 mg | |
| Maize starch | 90 mg | |
| sec calcium phosphate | 30 mg | |
| Soluble starch | 3 mg | |
| Magnesium stearate | 3 mg | |
| Colloidal silica | 4 mg | |
| | 200 mg | |
| (c) Active compound | 1 mg | |
| Lactose | 100 mg | |
| Maize starch | 60 mg | |
| sec calcium phosphate | 30 mg | |
| Soluble starch | 3 mg | |
| Magnesium stearate | 2 mg | |
| Colloidal silica | 4 mg | |
| | 200 mg | |

EXAMPLE C

Tablets can be prepared according to the following formulations:

| | |
|---|---|
| (a) Active compound | 2 mg |
| Lactose | 60 mg |
| Maize starch | 30 mg |
| Soluble starch | 4 mg |
| Magnesium stearate | 4 mg |
| | 100 mg |
| (b) Active compound | 24 mg |
| Lactose | 56 mg |
| Maize starch | 30 mg |
| Soluble starch | 5 mg |
| Magnesium stearate | 5 mg |
| | 120 mg |

EXAMPLE D

The following composition is suitable for the preparation of soft gelatin capsules containing 5 mg of active compound per capsule

| | |
|---|---|
| Active compound | 5 mg |
| Mixture of triglycerides from coconut oil | 150 mg |
| Capsule contents | 155 mg |

EXAMPLE E

The following recipes are suitable for the preparation of the contents of hard gelatin capsules:

| | |
|---|---|
| (a) Active compound | 10 mg |
| Maize starch | 190 mg |
| | 200 mg |
| (b) Active compound | 40 mg |
| Lactose | 80 mg |
| Maize starch | 80 mg |
| | 200 mg |

EXAMPLE F

Suppositories can be prepared by the following recipe:

| | |
|---|---|
| Active compound | 20 mg |
| Suppository foundation to | 2 g |

EXAMPLE G

Injection solutions can be prepared by the following recipes:

| | |
|---|---|
| (a) Active compound | 1.0 mg |
| Polyethylene glycol 400 | 0.3 mg |
| Sodium chloride | 2.7 mg |
| Water for injection to | 1 ml |
| (b) Active compound | 4.0 mg |
| Sodium chloride | 9.0 mg |
| Water for injection to | 1 ml |

EXAMPLE H

Drops can be prepared by the following recipe (20 mg of active compound in 1 ml = 20 drops):

| | |
|---|---|
| Active compound | 2.00 g |
| Methyl benzoate | 0.07 g |
| Ethyl benzoate | 0.03 g |
| Ethanol, 96% strength | 4 ml |
| Demineralized water to | 100 ml |

We claim:

1. 1,2,3,4-Oxatriazolium-5-substituted in the 3-position, of the general formula I

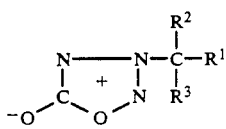

in which
R$^1$ denotes (C$_2$ to B$_4$) alkyl, R$^2$ denotes (C$_2$ to C$_4$) alkyl, and R$^3$ denotes (C$_1$ to C$_4$)alkyl.

2. 1,2,3,4-oxatriazolium-5-olate according to claim 1, characterized in that R$^1$ denotes ethyl.

3. 1,2,3,4-oxatriazolium-5-olate according to claim 1, characterized in that R$^3$ denotes methyl.

4. 3-tert-Pentyl-1,2,3,4-oxatriazolium-5-olate.

5. 3-(2-Methylpent-2-yl)-1,2,3,4-oxatriazolium-5-olate.

6. 3-(2,3-Dimethyl-but-2-yl)-1,2,3,4-oxatriazolium-5-olate.

7. 3-(3 methylpent-3-yl)-1,2,3,4-oxatriazolium-5-olate.

8. Method for providing antianginal or antithrombotic relief, which comprises administering an effective dose of a compound of claim 1 to a patient in need thereof.

9. Pharmaceutical preparation, characterized in that it contains a compound of claim 1 as active compound together with pharmaceutically acceptable excipients and additives and if desired one or more other pharmacological active compounds.

* * * * *

UNITED STATES PATENT AND TRADEMARK OFFICE
CERTIFICATE OF CORRECTION

PATENT NO. : 5,091,398
DATED : 2-25-92
INVENTOR(S) : Schonafinger et al.

It is certified that error appears in the above—identified patent and that said Letters Patent is hereby corrected as shown below:

Col. 1, line 18, "$(D_2$ to $D_4)$" should read --$(C_2$ to $C_4)$--;

Col. 11, line 15, before "substituted" insert --olate--;

Col. 12, line 2, "$(C_2$ to $B_4)$" should read --$(C_2$ to $C_4)$--;

Col. 12, line 13, "3 methylpent" should read --(3-Methylpent--.

Signed and Sealed this

Third Day of August, 1993

Attest:

MICHAEL K. KIRK

Attesting Officer

Acting Commissioner of Patents and Trademarks